United States Patent
Kawasaki et al.

(10) Patent No.: US 11,974,770 B2
(45) Date of Patent: May 7, 2024

(54) MEDICAL DEVICE SYSTEM, ABNORMALITY DETERMINATION METHOD, AND COMPUTER-READABLE RECORDING MEDIUM

(71) Applicant: OLYMPUS CORPORATION, Tokyo (JP)

(72) Inventors: Minoru Kawasaki, Tokyo (JP); Masashi Yamada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 795 days.

(21) Appl. No.: 17/065,032

(22) Filed: Oct. 7, 2020

(65) Prior Publication Data

US 2021/0015516 A1 Jan. 21, 2021

Related U.S. Application Data (63) Continuation of application No. PCT/JP2018/015453, filed on Apr. 12, 2018.

(51) Int. Cl.
*A61B 17/32* (2006.01)
*A61B 17/00* (2006.01)
*A61B 18/00* (2006.01)

(52) U.S. Cl.
CPC ........... *A61B 17/320068* (2013.01); *A61B 17/320092* (2013.01); *A61B 2017/00119* (2013.01);
(Continued)

(58) Field of Classification Search
CPC .... A61B 17/320068; A61B 17/320092; A61B 2017/320082; A61B 2017/00119;
(Continued)

(56) References Cited

U.S. PATENT DOCUMENTS 9,597,106 B2   3/2017   Tsubuku
2005/0033201 A1  2/2005   Takahashi et al.
(Continued)

FOREIGN PATENT DOCUMENTS

CN   105916459 A   8/2016
JP   2001-212514 A   8/2001
(Continued)

OTHER PUBLICATIONS

Jun. 26, 2018 Search Report issued in International Patent Application No. PCT/JP2018/015453.
(Continued)

*Primary Examiner* — Tuan V Nguyen
(74) *Attorney, Agent, or Firm* — Oliff PLC (57) ABSTRACT

A medical device system that includes an ultrasound transducer and a processor. The ultrasound transducer includes a plurality of electrode plates to which a drive signal is supplied, and a plurality of piezoelectric elements that are alternately arranged with the electrode plates, and that generate ultrasound vibrations according to the drive signal. The ultrasound transducer also includes an electric wiring that electrically connects the electrode plates adjacent to each other, and a memory that stores reference information regarding specific initial characteristics. The processor analyzes the generated ultrasonic vibrations to determine a resonance point of the ultrasound transducer, and detects resonance point information regarding the resonance point. The processor then determines whether an abnormality has occurred in the ultrasound transducer by comparing the stored reference information and the detected resonance point information.

11 Claims, 8 Drawing Sheets

(52) U.S. Cl.
CPC ........... *A61B 2017/00402* (2013.01); *A61B 2017/320082* (2017.08); *A61B 2018/00589* (2013.01); *A61B 2018/00607* (2013.01)

(58) Field of Classification Search
CPC ........... A61B 2017/00402; A61B 2018/00589; A61B 2018/00607
See application file for complete search history.

(56) References Cited

U.S. PATENT DOCUMENTS

| | | |
|---|---|---|
| 2005/0070800 A1 | 3/2005 | Takahashi |
| 2016/0256190 A1* | 9/2016 | Tsubuku ........ A61B 17/320092 |

FOREIGN PATENT DOCUMENTS

| | | |
|---|---|---|
| JP | 2003-339730 A | 12/2003 |
| JP | 2005-66316 A | 3/2005 |
| JP | 2005-102811 A | 4/2005 |
| JP | 2010-34817 A | 2/2010 |
| JP | 2015-208711 A | 11/2015 |

OTHER PUBLICATIONS

Oct. 28, 2023 Office Action issued in Chinese Application No. 201880092220.8.

* cited by examiner

MEDICAL DEVICE SYSTEM, ABNORMALITY DETERMINATION METHOD, AND COMPUTER-READABLE RECORDING MEDIUM

CROSS-REFERENCE TO RELATED APPLICATION

This application is a continuation of International Application No. PCT/JP2018/015453, filed on Apr. 12, 2018, the entire contents of which are incorporated herein by reference.

BACKGROUND

Related Art

In the related art, a medical device system includes an ultrasound transducer that generates ultrasound vibrations according to a drive signal and a control device that outputs the drive signal to the ultrasound transducers, and the medical device system treats a living tissue by applying the ultrasound vibrations to the living tissue.

SUMMARY

In some embodiments, a medical device system includes an ultrasound transducer including: a plurality of electrode plates to which a drive signal is supplied, a plurality of piezoelectric elements alternately arranged with respect to the plurality of electrode plates, the plurality of piezoelectric elements being configured to generate ultrasound vibrations according to the drive signal, an electric wiring configured to electrically connect the plurality of electrode plates, which are adjacent to each other, and a memory configured to store reference information regarding specific initial characteristics; and a processor operatively coupled to the ultrasound transducer, the processor being configured to: analyze the generated ultrasonic vibrations to determine a resonance point of the ultrasound transducer, detect resonance point information regarding the determined resonance point, and determine whether an abnormality has occurred in the ultrasound transducer by comparing the stored reference information and the detected resonance point information.

In some embodiments, provided is an abnormality determination method executed by a processor of a medical device system including i) a plurality of electrode plates to which a drive signal is supplied, (ii) a plurality of piezoelectric elements alternately arranged with respect to the plurality of electrode plates, where the plurality of electrode plates are configured to generate ultrasound vibrations according to the drive signal, (iii) an electric wiring configured to electrically connect the plurality of electrode plates, which are adjacent to each other, and (iv) a memory storing reference information regarding specific initial characteristics. The abnormality determination method includes analyzing the generated ultrasonic vibrations to determine a resonance point of the ultrasound transducer, detecting resonance point information regarding the detected resonance point, and determining whether an abnormality has occurred in the ultrasound transducer by comparing the stored reference information and the detected resonance point information.

In some embodiments, provided is a non-transitory computer-readable recording medium with an executable program stored thereon. The program is an abnormality determination program executed by a processor of a medical device system including an ultrasound transducer, which includes (i) a plurality of electrode plates to which a drive signal is supplied, (ii) a plurality of piezoelectric elements alternately arranged with respect to the plurality of electrode plates, wherein the plurality of piezoelectric elements are configured to generate ultrasound vibrations according to the drive signal, (iii) an electric wiring configured to electrically connect the plurality of electrode plates adjacent to each other, and (iv) a memory configured to store reference information regarding specific initial characteristics. The abnormality determination program causes the processor to execute analyzing the generated ultrasonic vibrations to determine a resonance point of the ultrasound transducer, detecting resonance point information regarding the determined resonance point, and determining whether an abnormality has occurred in the ultrasound transducer by comparing the stored reference information and the detected resonance point information.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, a mode (hereinafter, "embodiment") for carrying out the disclosure will be described with reference to the accompanying drawings. Note that the disclosure is not limited to embodiments described below. Furthermore, in the drawings, the same components are denoted with the same reference numerals.

First Exemplary Embodiment

Schematic Configuration of Medical Device System

Figure 1:
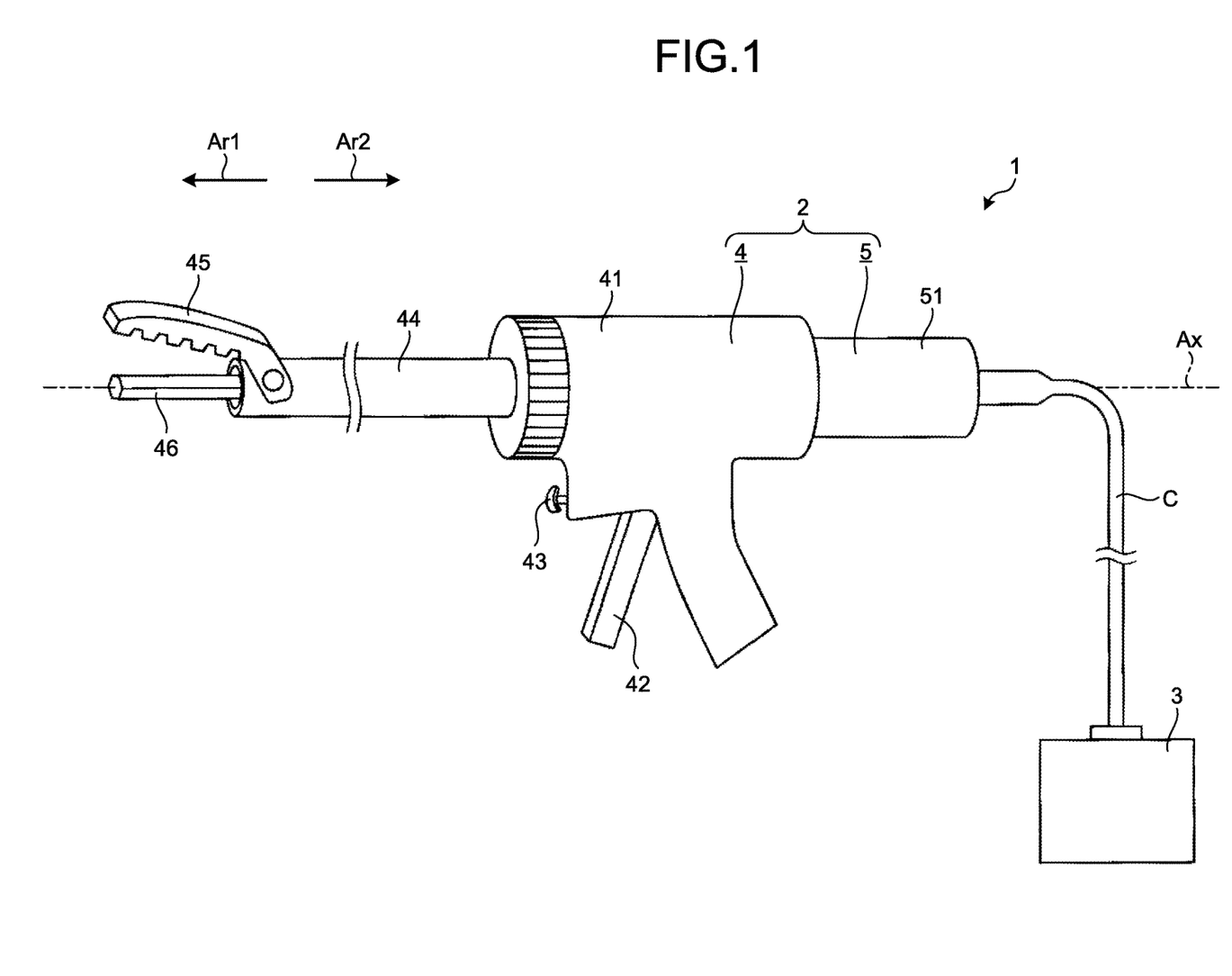
FIG. 1 is a view illustrating a medical device system according to an exemplary embodiment.
Figure 2:
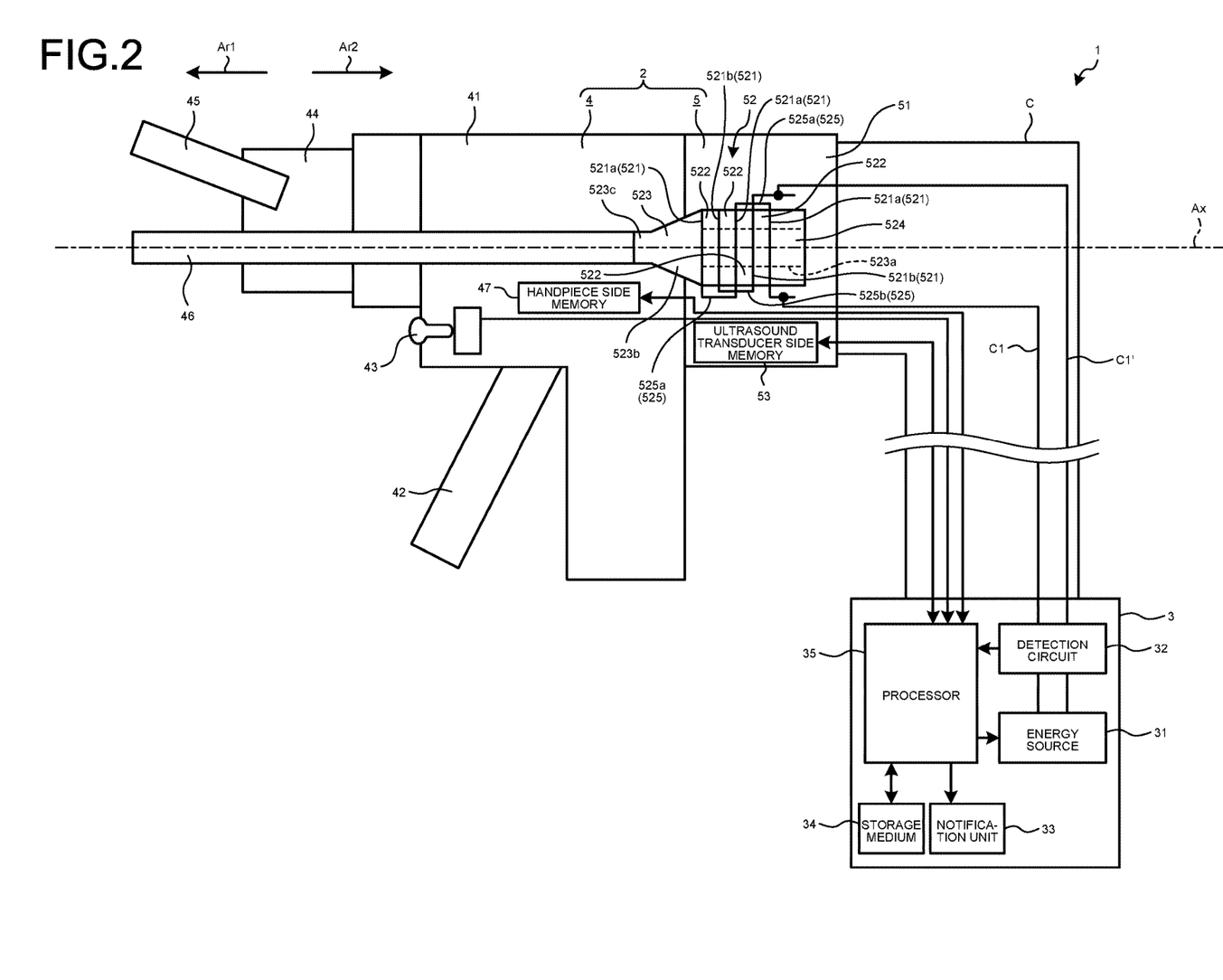
FIG. 2 is a view illustrating an internal configuration of a treatment tool and a control device.

FIG. 1 is a view illustrating a medical device system 1 according to the first exemplary embodiment. FIG. 2 is a view illustrating an internal configuration of a treatment tool 2 and a control device 3.

The medical device system 1 treats a target site by applying ultrasound energy to a site (hereinafter, referred to as the target site) to be treated in a biological tissue. Here, the treatment means, for example, coagulation and incision of the target site. As illustrated in FIGS. 1 and 2, the medical device system 1 includes a treatment tool 2 and a control device 3.

Configuration of Treatment Tool

The treatment tool 2 is, for example, a medical treatment tool using BLT (Bolt-clamped Langevin type Transducer) for treating the target site while passing through an abdominal wall. The treatment tool 2 includes a handpiece 4 and an ultrasound transducer 5, as illustrated in FIGS. 1 and 2.

As illustrated in FIGS. 1 and 2, the handpiece 4 includes a holding case 41, an operation knob 42, a switch 43, a sheath 44, a jaw 45, an ultrasound probe 46, and a handpiece side memory 47 (FIG. 2).

The holding case 41 supports the entirety of the treatment tool 2.

The operation knob 42 is movably attached to the holding case 41 and receives an opening/closing operation by an operator.

The switch 43 is provided so as to be exposed to the outside of the holding case 41, and receives an output start operation by the operator. Then, the switch 43 outputs an operation signal corresponding to the output start operation to the control device 3.

The sheath 44 has a cylindrical shape. Note that in the following, a central axis of the sheath 44 will be referred to as a central axis Ax (FIGS. 1 and 2). Note that in the following, one side along the central axis Ax will be referred to as a distal end side Ar1 (FIGS. 1 and 2), and the other side will be referred to as a proximal end side Ar2 (FIGS. 1 and 2). Then, the sheath 44 is attached to the holding case 41 by inserting a portion of the proximal end side Ar2 into the holding case 41 from the distal end side Ar1 of the holding case 41.

The jaw 45 is rotatably attached to an end portion of the distal end side Ar1 in the sheath 44 and holds the target site between the jaw 45 and a portion of the distal end side Ar1 of the ultrasound probe 46. Note that an opening/closing mechanism (not illustrated) for opening and closing the jaw 45 with respect to the portion of the distal end side Ar1 of the ultrasound probe 46 according to the opening/closing operation of the operation knob 42 by the operator is provided inside the holding case 41 and the sheath 44 described above.

The ultrasound probe 46 has a long shape that linearly extends along the central axis Ax, and is inserted into the sheath 44 in a state in which the portion of the distal end side Ar1 protrudes outward as illustrated in FIGS. 1 and 2. In addition, the end portion of the ultrasound probe 46 on the proximal end side Ar2 is connected to a BLT 52 (FIG. 2) that constitutes the ultrasound transducer 5. Then, the ultrasound probe 46 transmits ultrasound vibration generated by the BLT 52 from the end portion of the proximal end side Ar2 to the end portion of the distal end side Ar1. In the first embodiment, the ultrasound vibration is longitudinal vibration that vibrates in a direction along the central axis Ax. At this time, the portion of the distal end side Ar1 of the ultrasound probe 46 vibrates with an amplitude of, for example, 80 μm due to the longitudinal vibration of the ultrasound probe 46. That is, the ultrasound vibration is applied to the target site grasped between the jaw 45 and the portion of the distal end side Ar1 of the ultrasound probe 46 from the portion of the distal end side Ar1. In other words, ultrasound energy is applied to the target site from the portion of the distal end side Ar1. As a result, frictional heat is generated between the portion of the distal end side Ar and the target site. Then, the target site is treated.

The handpiece side memory 47 stores probe type information indicating the type of the ultrasound probe 46.

As illustrated in FIGS. 1 and 2, the ultrasound transducer 5 includes an ultrasound transducer case 51, the BLT 52 (FIG. 2), and an ultrasound transducer side memory 53 (FIG. 2).

The ultrasound transducer case 51 supports the BLT 52 and the ultrasound transducer side memory 53, and is detachably connected to the holding case 41.

The BLT 52 generates ultrasound vibration under the control of the control device 3. As illustrated in FIG. 2, the BLT 52 includes a plurality of electrode plates 521, a plurality of piezoelectric elements 522, a front mass 523, and an electric wiring 525.

The plurality of electrode plates 521 are portions to which drive signals are supplied from the control device 3. Note that in an example of FIG. 2, five electrode plates 521 are illustrated. The plurality of electrode plates 521 each have a disk shape having an opening in the center, and are arranged in parallel along the central axis Ax. In addition, the plurality of electrode plates 521 includes negative electrode plates 521a that function as negative electrodes and positive electrode plates 521b that function as positive electrodes. Then, the negative electrode plates 521a and the positive electrode plates 521b are arranged alternately along the central axis Ax.

The plurality of piezoelectric elements 522 each have a disk shape having an opening in the center, and are arranged between the negative electrode plate 521a and the positive electrode plate 521b. That is, the plurality of electrode plates 521 and the plurality of piezoelectric elements 522 are alternately arranged along the central axis Ax. Note that in the example of FIG. 2, four piezoelectric elements 522 are illustrated. When alternately arranging the plurality of piezoelectric elements 522, an amplitude characteristic with respect to a resonance frequency of the BLT 52 is set within a predetermined range in consideration of variations in characteristics of the plurality of piezoelectric elements 522. Specifically, an Ak value which is an evaluation index described in International Publication No. 2013/027614 and a C1 value which is an evaluation index formed from capacitances, anti-resonance frequencies, and resonance frequencies of the plurality of piezoelectric elements 522 are used to select the plurality of piezoelectric elements 522. Then, the plurality of piezoelectric elements 522 generate ultrasound vibration of longitudinal vibration having a direction along the central axis Ax as a vibration direction when a potential difference is generated in a thickness direction along the central axis Ax according to the drive signals supplied to the plurality of electrode plates 521.

The front mass 523 expands the amplitude of the ultrasound vibration generated by the plurality of piezoelectric elements 522. The front mass 523 has a long shape that linearly extends along the central axis Ax. Then, the front mass 523 includes an element mounting portion 523a, a cross-sectional area changing portion 523b, and a probe mounting portion 523c, as illustrated in FIG. 2.

The element mounting portion 523a is a bolt that linearly extends along the central axis Ax, and is inserted into each central opening of the plurality of electrode plates 521 and the plurality of piezoelectric elements 522. Then, as illustrated in FIG. 2, a back mass 524 is attached to an end portion of the proximal end side Ar2 in the element mounting portion 523a.

The cross-sectional area changing portion (horn) 523b is a portion which is provided at the end portion of the distal end side Ar1 in the element mounting portion 523a and which enlarges the amplitude of the ultrasound vibration. As illustrated in FIG. 2, the cross-sectional area changing portion 523b has a truncated cone shape whose end portion of the proximal end side Ar2 is set to have a larger diameter dimension than the element mounting portion 523a and whose cross-sectional area decreases toward the distal end side Ar1. That is, the plurality of electrode plates 521 and the plurality of piezoelectric elements 522 are integrated with each other to have a substantially cylindrical shape by being sandwiched between the cross-sectional area changing portion 523b and the back mass 524.

As illustrated in FIG. 2, the probe mounting portion 523c is provided at an end portion of the distal end side Ar1 in the cross-sectional area changing portion 523b and extends linearly along the central axis Ax. Then, the end portion of the distal end side Ar1 in the probe mounting portion 523c is connected to the end portion of the proximal end side Ar2 in the ultrasound probe 46 in a state in which the ultrasound transducer 5 is connected to the handpiece 4.

The electric wiring 525 is a portion that electrically connects the electrode plates 521 adjacent to each other. As illustrated in FIG. 2, the electric wiring 525 includes a negative electrode wiring 525a that electrically connects the negative electrode plates 521a adjacent to each other, and a positive electrode wiring 525b that electrically connects the positive electrode plates 521b adjacent to each other. Here, the electric wiring 525 is provided on an outer periphery of the substantially cylindrical shape of the plurality of electrode plates 521 and the plurality of piezoelectric elements 522 integrated with each other.

The ultrasound transducer side memory 53 corresponds to a memory. The ultrasound transducer side memory 53 stores transducer type information and reference information.

The transducer type information is information indicating the type of BLT 52.

The reference information is information about initial characteristics specific to the BLT 52, which is measured when a product of the treatment tool 2 is shipped. In the first embodiment, the reference information is information indicating the resonance frequency of BLT 52.

Configuration of Control Device

The treatment tool 2 is detachably connected to the control device 3 by an electric cable C (FIG. 1). Then, the control device 3 comprehensively controls an operation of the treatment tool 2 by passing through the electric cable C. As illustrated in FIG. 2, the control device 3 includes an energy source 31, a detection circuit 32, a notification unit 33, a storage medium 34, and a processor 35.

Here, a pair of lead wires C1 and C1' that constitute the electric cable C are respectively joined to the negative electrode plate 521a located on the most proximal end side Ar2 among the plurality of negative electrode plates 521a, and the positive electrode plate 521b located on the most proximal end side Ar2 among the plurality of positive electrode plates 521b.

Then, the energy source 31 outputs a drive signal, which is alternating current power, to the plurality of negative electrode plates 521a and the plurality of positive electrode plates 521b through the pair of lead wires C1 and C1' under the control of the processor 35. This causes the BLT 52 to generate the ultrasound vibration.

The detection circuit 32 detects a voltage phase signal θV (hereinafter, referred to as a voltage phase signal θV), a current phase signal θI (hereinafter, referred to as a current phase signal θI), and a current value I in the drive signal output from the energy source 31. Then, the detection circuit 32 outputs the detected phase signals θV and θI and the current value I to the processor 35.

The notification unit 33 notifies predetermined information under the control of the processor 35. Examples of the notification unit 33 may include, for example, a light emitting diode (LED) that notifies predetermined information by lighting or blinking or a color when lighting, a display device that displays the predetermined information, a speaker that outputs the predetermined information by voice, and the like.

The storage medium 34 stores a program (including an abnormality determination program) executed by the processor 35, information necessary for treatment of the processor 35, and the like. Here, examples of the information necessary for the processing of the processor 35 may include threshold information, sweep information, control target information, design range information, and the like.

The threshold information is information indicating a threshold for determining an abnormality of the BLT 52.

The sweep information is information indicating a sweep start drive frequency and a sweep end drive frequency when sweeping a frequency (hereinafter referred to as a drive frequency) of the drive signal output from the energy source 31.

The control target information is information indicating the types of the ultrasound probe 46 and the BLT 52 that can be controlled.

The design range information is information indicating a prescribed range including a design anti-resonance point with reference to a design resonance frequency of the BLT 52. The range may be, for example, a range of 46.5 [kHz] to 47.5 [kHz].

Figure 3:
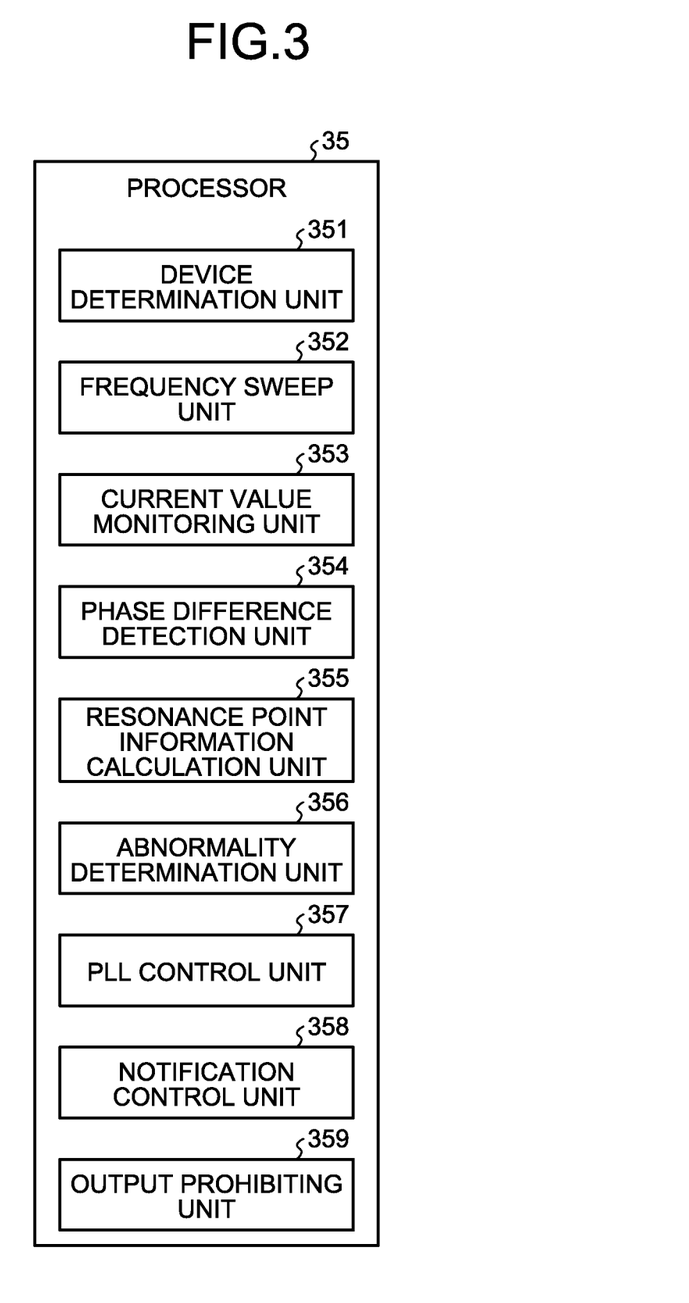
FIG. 3 is a block diagram illustrating functions of a processor.

FIG. 3 is a block diagram illustrating functions of the processor 35.

The processor 35 is, for example, a central processing unit (CPU), a field-programmable gate array (FPGA), or the like, and is electrically connected to the switch 43, the handpiece side memory 47, and the ultrasound transducer side memory 53 in a state in which the treatment tool 2 is connected to the control device 3 by the electric cable C. Then, the processor 35 controls the operation of an entirety of the medical device system 1 according to the program stored in the storage medium 34. As illustrated in FIG. 3, the processor 35 includes a device determination unit 351, a frequency sweep unit 352, a current value monitoring unit 353, a phase difference detection unit 354, a resonance point information calculation unit 355, an abnormality determination unit 356, a phase lock loop (PLL) control unit 357, a notification control unit 358, and an output prohibiting unit 359.

The device determination unit 351 determines whether the treatment tool 2 connected to the control device 3 is a controllable treatment tool 2 based on the probe type information and the transducer type information stored in the treatment tool 2 and the control target information stored in the storage medium 34.

The frequency sweep unit 352 controls an operation of the energy source 31 based on the sweep information stored in the storage medium 34, and sweeps the drive frequency.

The current value monitoring unit 353 monitors the current value I output from the detection circuit 32.

The phase difference detection unit 354 detects a phase difference (θV-θI) between the voltage and the current of the drive signal output from the energy source 31, based on the phase signals θV and θI output from the detection circuit 32.

The resonance point information calculation unit 355 calculates resonance point information regarding the resonance point of the BLT 52 based on a detection result by the phase difference detection unit 354. In the first embodiment, the resonance point information is the resonance frequency of BLT 52.

The abnormality determination unit 356 determines whether or not an abnormality has occurred in the BLT 52 based on the resonance point information calculated by the resonance point information calculation unit 355, the reference information stored in the ultrasound transducer side memory 53, and the threshold information stored in the storage medium 34. In the first embodiment, the abnormality determination unit 356 determines whether or not a disconnection has occurred in the electric wiring 525.

The PLL control unit 357 controls the operation of the energy source 31 based on the detection result of the phase difference detection unit 354, and executes a PLL control for locking the drive frequency to the resonance frequency calculated by the resonance point information calculation unit 355.

The notification control unit 358 controls an operation of the notification unit 33 based on the determination results of the device determination unit 351 and the abnormality determination unit 356, and causes the notification unit 33 to notify predetermined information.

The output prohibiting unit 359 controls the operation of the energy source 31 based on the determination results of the device determination unit 351 and the abnormality determination unit 356, and prohibits the output of the drive signal from the energy source 31. That is, the output prohibiting unit 359 prohibits the output of ultrasound energy from the ultrasound probe 46 to the target site.

Abnormality Determination Method

Next, an abnormality determination method executed by the processor 35 described above will be described.

Figure 4:
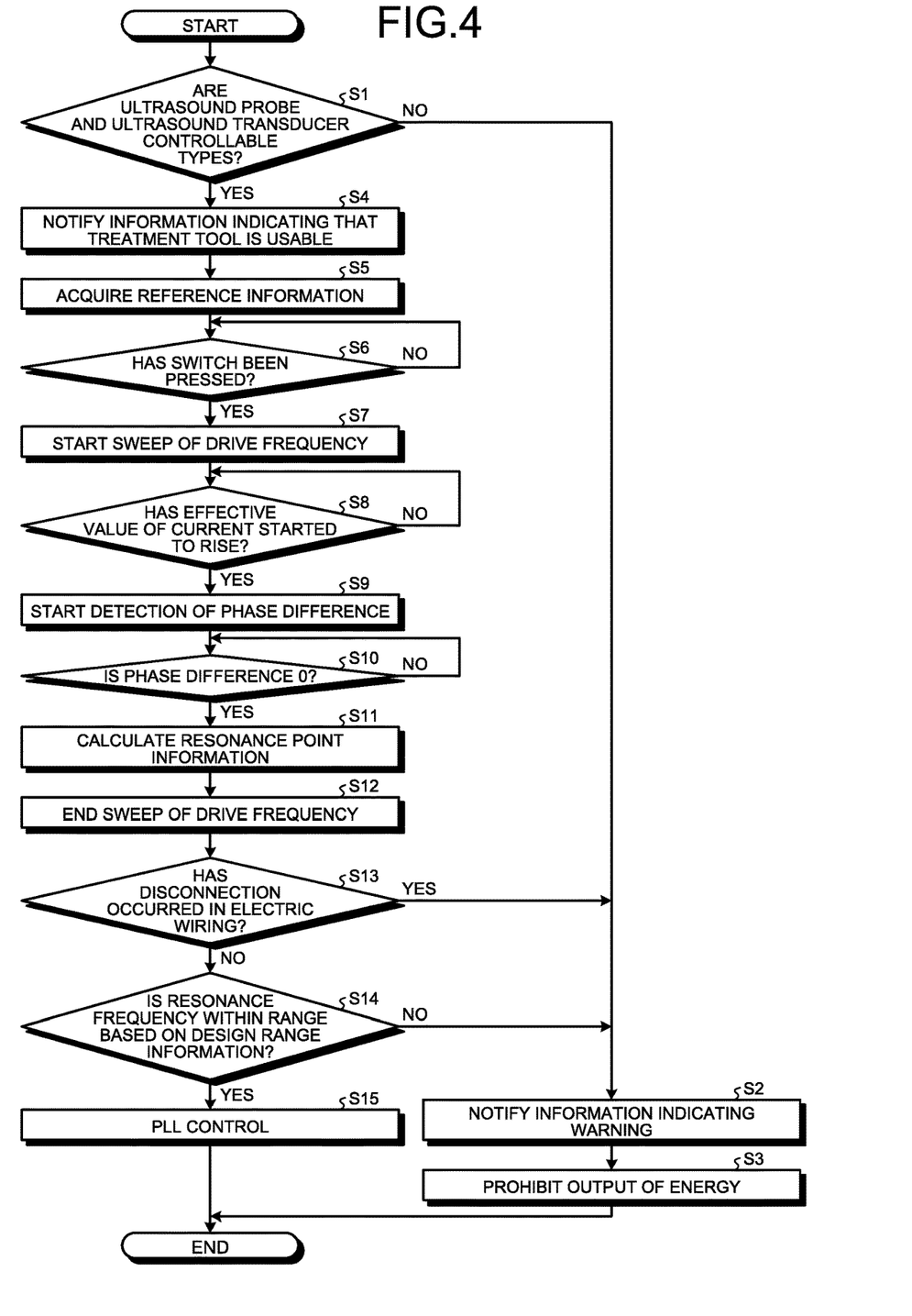
FIG. 4 is a flowchart illustrating an abnormality determination method executed by the processor.

FIG. 4 is a flowchart illustrating an abnormality determination method executed by the processor 35.

First, when the treatment tool 2 is connected to the control device 3 by the electric cable C, the device determination unit 351 reads the probe type information and the transducer type information from the handpiece side memory 47 and the ultrasound transducer side memory 53, respectively. The device determination unit 351 also reads the control target information from the storage medium 34. Then, the device determination unit 351 determines whether or not the ultrasound probe 46 and the BLT 52 that constitute the treatment tool 2 connected to the control device 3 are controllable types based on the probe type information, the transducer type information, and the control target information (Step S1).

If it is determined that the type is uncontrollable (Step S1: No), the notification control unit 358 causes the notification unit 33 to notify information indicating a warning (Step S2). For example, the notification control unit 358 causes the notification unit 33 to notify information indicating that the ultrasound probe 46 and the BLT 52 that constitute the treatment tool 2 connected to the control device 3 are uncontrollable types, as the information indicating the warning.

After step S2, the output prohibiting unit 359 prohibits the output of the drive signal from the energy source 31 (Step S3). Then, the processor 35 ends the abnormality determination method.

On the other hand, if it is determined that the type is controllable (Step S1: Yes), the notification control unit 358 causes the notification unit 33 to notify information indicating that the treatment tool 2 can be used (Step S4).

After step S4, the abnormality determination unit 356 reads the reference information stored in the ultrasound transducer side memory 53 (Step S5).

The operator recognizes that the treatment tool 2 can be used by the notification in step S4, and then inserts the portion of the distal end side Ar1 in the treatment tool 2 into an abdominal cavity through an abdominal wall using, for example, a trocar. Then, the operator opens and closes the operation knob 42 to grasp the target site by the jaw 45 and the portion of the distal end side Ar1 in the ultrasound probe 46. Then, the operator presses the switch 43 (Step S6: Yes).

If the switch 43 is pressed (Step S6: Yes), the frequency sweep unit 352 causes the energy source 31 to output the drive signal based on the sweep information stored in the storage medium 34, and starts a drive frequency sweep (Step S7). Then, in step S7, a search for the resonance point of the BLT 52 is started.

Figure 5:
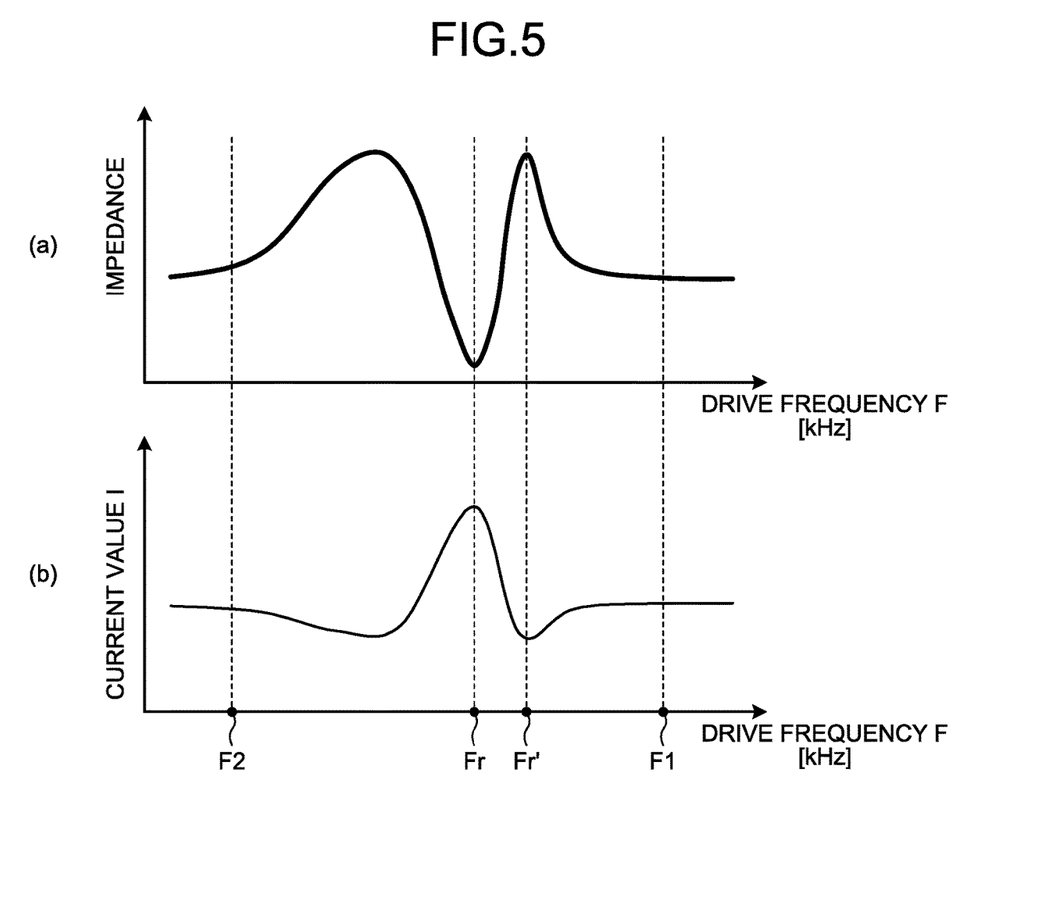
FIG. 5 is a view illustrating a method of searching for a resonance point.

FIG. 5 is a view illustrating a method of searching for a resonance point. Specifically, FIG. 5(a) is a view illustrating frequency characteristics of impedance in the BLT 52. FIG. 5(b) is a view illustrating a behavior of the current value I in the drive signal when the drive frequency F is swept in step S7.

Specifically, the frequency sweep unit 352 reduces a drive frequency F from a sweep start drive frequency F1 (FIG. 5) to a sweep end drive frequency F2 (FIG. 5), based on the sweep information stored in the storage medium 34. Note that the range from the drive frequency F2 to the drive frequency F1 is a range including the design resonance point and anti-resonance point of the BLT 52.

After step S7, the current value monitoring unit 353 constantly monitors whether or not the current value I output from the detection circuit 32 has started to rise (Step S8). As illustrated in FIG. 5(b), when the drive frequency F exceeds an anti-resonance point Fr' by sweeping the drive frequency F, the current value I in the drive signal output from the energy source 31 starts to rise. That is, the current value monitoring unit 353 constantly monitors in step S8 whether the drive frequency F exceeds the anti-resonance point Fr'.

If it is determined that the current value I has started to rise (Step S8: Yes), the phase difference detection unit 354 starts the detection of the phase difference ($\theta V$-$\theta I$) between the voltage and the current of the drive signal output from the energy source 31 based on the respective phase signals $\theta V$ and $\theta I$ output from the detection circuit 32 (Step S9). Then, the phase difference detection unit 354 constantly monitors whether or not the phase difference becomes 0 (Step S10). Although not specifically illustrated, the phase difference becomes 0 at the resonance frequency Fr of the BLT 52 which is the drive frequency F at the time when the current value I reaches the maximum value. That is, the phase difference detection unit 354 detects a point where the drive frequency F becomes the resonance frequency Fr of the BLT 52 as a result of sweeping the drive frequency F in step S10.

If it is determined that the phase difference has become 0 (Step S10: Yes), the resonance point information calculation unit 355 calculates the resonance frequency Fr of the BLT 52 that is the drive frequency F at the time when the phase difference becomes 0, as resonance point information (Step S11). In addition, the frequency sweep unit 352 ends the sweep of the drive frequency F (Step S12).

After step S12, the abnormality determination unit 356 determines whether or not a disconnection has occurred in the electric wiring 525 based on the resonance frequency Fr of the BLT 52 calculated in step S11, the resonance frequency measured at the time of shipping of the product of the BLT 52 based on the reference information read in step S5, and the threshold information stored in the storage medium 34 (Step S13), and in the following, for convenience of description, the resonance frequency Fr of the BLT 52 calculated in step S11 is described as a current resonance frequency Fr, and the resonance frequency measured at the time of shipping of the product of the BLT 52 based on the reference information is described as an initial resonance frequency.

Figure 6:
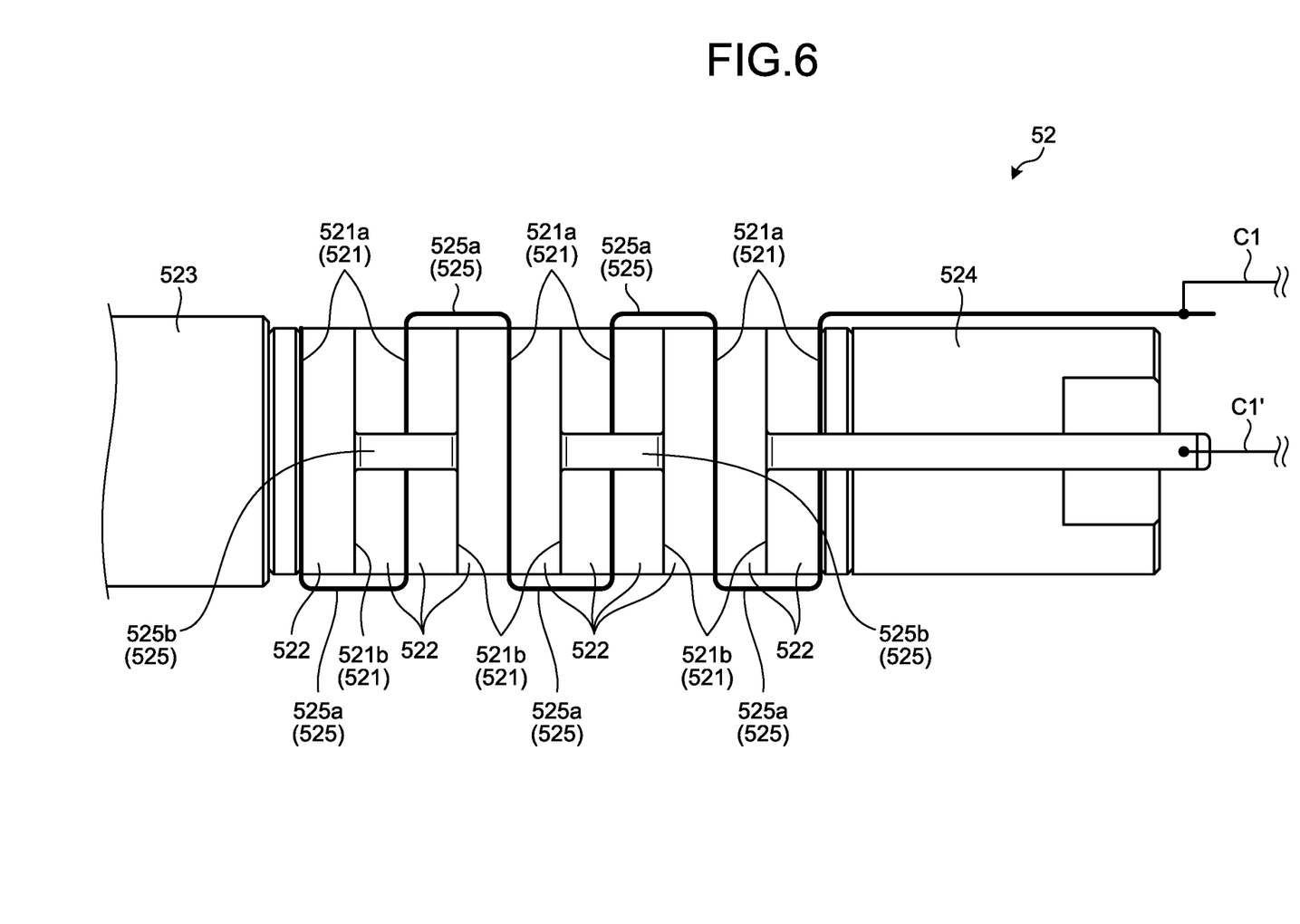
FIG. 6 is a view illustrating a state in which a disconnection has occurred in an electric wiring.
Figure 7:
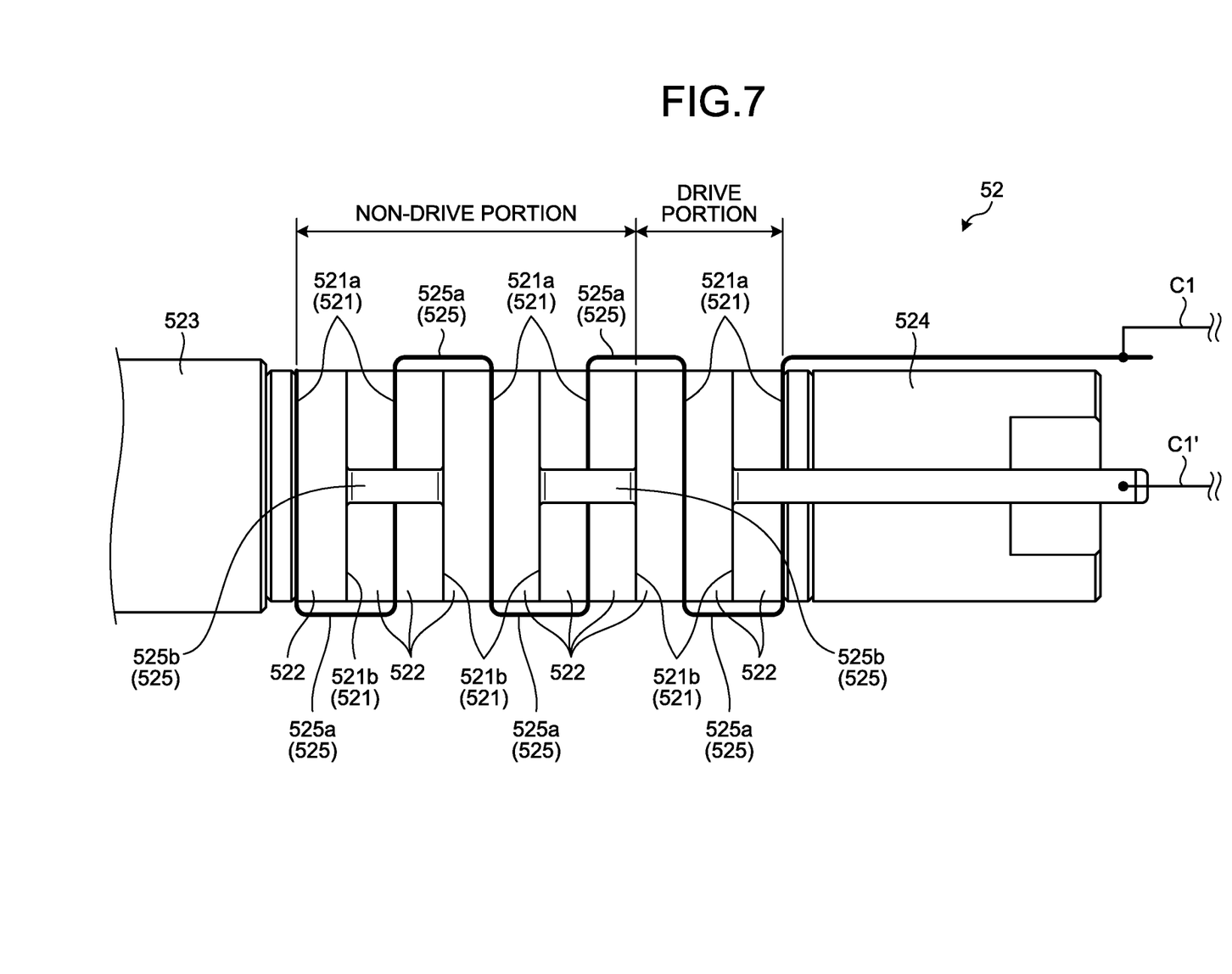
FIG. 7 is a view illustrating a state in which a disconnection has occurred in an electric wiring.

FIGS. 6 and 7 are views illustrating states in which a disconnection has occurred in the electric wiring 525. Note that in the example of FIGS. 6 and 7, unlike the example of FIG. 2, eleven electrode plates 521 and ten piezoelectric elements 522 are illustrated.

Here, as illustrated in FIG. 6, when the disconnection has not occurred in the electric wiring 525, the following state occurs.

That is, when the drive signal is output to the plurality of negative electrode plates 521a and the plurality of positive electrode plates 521b via the pair of lead wires C1 and C1', the ten piezoelectric elements 522 are driven because a potential difference occurs.

On the other hand, as illustrated in FIG. 7, when the disconnection has occurred in the second negative electrode wiring 525a from the proximal end side Ar2 that is a portion of the electric wiring 525, the following state occurs.

That is, when the drive signal is output to the plurality of negative electrode plates 521a and the plurality of positive electrode plates 521b via the pair of lead wires C1 and C1', some of the ten piezoelectric elements 522 do not drive because no potential difference occurs. In addition, other piezoelectric elements 522 are driven because the potential difference occurs. Then, when only some of all the piezoelectric elements 522 are driven, the portion of the distal end side Ar1 in the ultrasound probe 46 does not vibrate at a desired amplitude of, for example, 80 µm, but vibrates with another amplitude. That is, the treatment performance of the target site is lowered.

Therefore, in order to prevent the treatment of the target site from being performed in the state in which the treatment performance is lowered, it is determined in step S13 whether or not the disconnection has occurred in the electric wiring 525.

Figure 8:
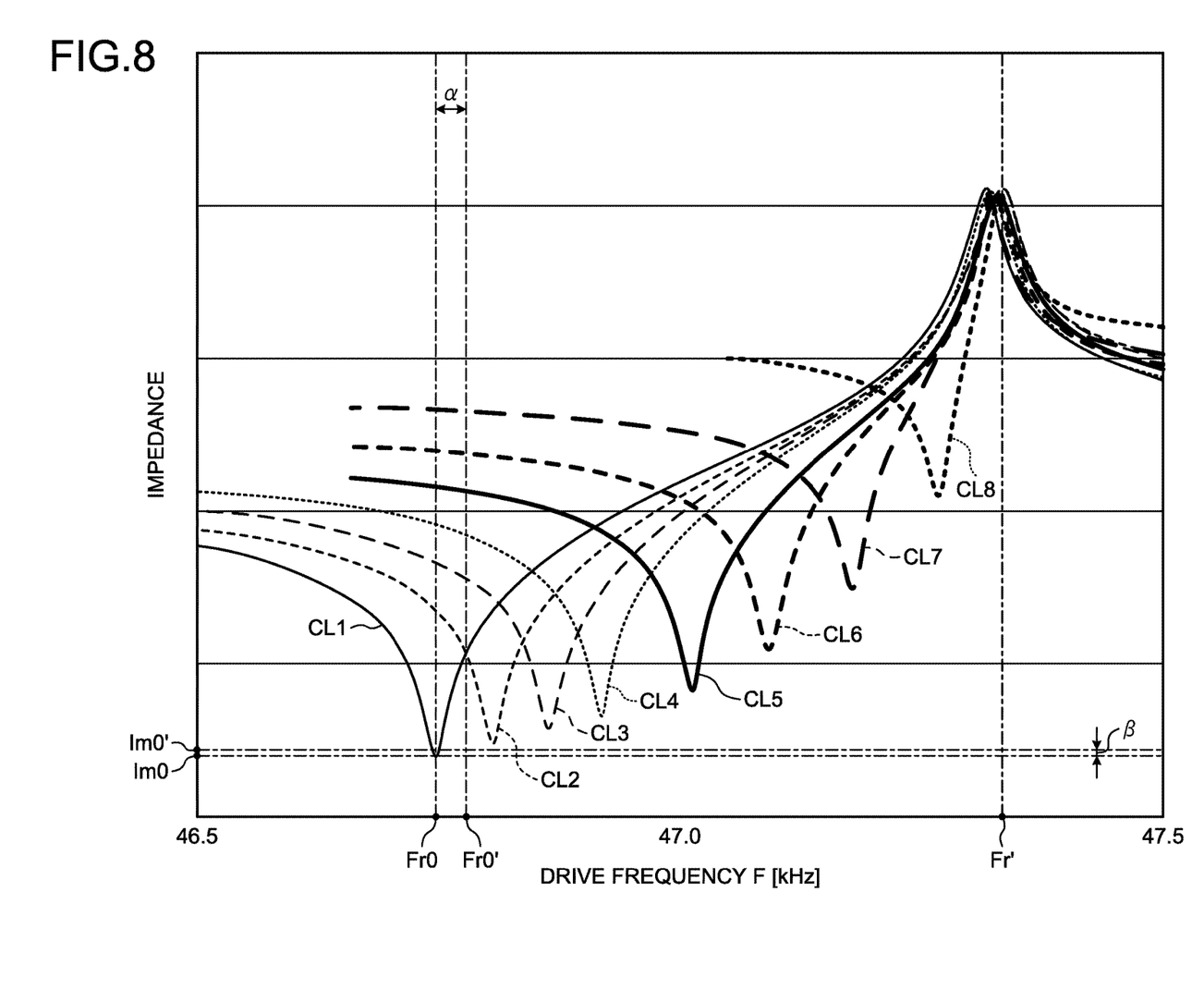
FIG. 8 is a view illustrating a method of determining a disconnection of an electric wiring.

FIG. 8 is a view illustrating a method of determining a disconnection of an electric wiring 525. Specifically, FIG. 8 is a view illustrating a change in frequency characteristics of impedance due to the disconnection occurring in the electric wiring 525. Note that FIG. 8 illustrates a case in which the total number of piezoelectric elements 522 is eight. Then, a curve CL1 illustrates a frequency characteristic of impedance when the disconnection has not occurred in the electric wiring 525 and all eight piezoelectric elements 522 are driven. In addition, a curve CL2 illustrates a frequency characteristic of impedance when the disconnection has occurred in the electric wiring 525 and only the seven piezoelectric elements 522 are driven. Further, curves CL3 to CL8 illustrate frequency characteristics of impedance when only 6 to 1 piezoelectric elements 522 are driven, respectively.

By the way, as the number of the driven piezoelectric elements 522 decreases, the frequency characteristic of impedance hardly changes at the anti-resonance point as illustrated in FIG. 8, but the resonance point and the impedance gradually increase. Note that the change in the frequency characteristic of the impedance occurs due to the following reasons.

The Young's modulus in terms of acoustic characteristics is a distortion of a substance generated when an external force is applied. Since the piezoelectric element 522 actively distorts itself, the distortion is likely to occur in terms of the acoustic characteristics. In other words, the piezoelectric element 522 behaves as a material having a low Young's modulus. On the other hand, the piezoelectric element 522 which is not driven due to the disconnection of the electric wiring 525 does not generate active distortion, and is therefore regarded as a material having a high Young's modulus. That is, as the number of driven piezoelectric elements 522 decreases, the Young's modulus increases, and the above-described change occurs.

Then, in step S13, focused on the change in the frequency characteristics of the impedance illustrated in FIG. 8, it is determined whether or not the disconnection has occurred in the electric wiring 525.

Specifically, in step S13, the abnormality determination unit 356 determines whether or not the current resonance frequency Fr is in the range between an initial resonance frequency Fr0 (FIG. 8) and a frequency Fr0' obtained by adding a threshold α (FIG. 8) based on the threshold information to the initial resonance frequency Fr0. Then, the abnormality determination unit 356 determines that the disconnection has not occurred in the electric wiring 525 when the current resonance frequency Fr is within the range, and determines that the disconnection has occurred in the electric wiring 525 when the current resonance frequency Fr is outside the range.

If it is determined that the disconnection has occurred in the electric wiring 525 (Step S13: Yes), the processor 35 proceeds to step S2. Then, in step S2, the notification control unit 358 causes the notification unit 33 to notify information indicating that the disconnection has occurred in the electric wiring 525, as the information indicating the warning.

On the other hand, if it is determined that the disconnection has not occurred in the electric wiring 525 (Step S13: No), the processor 35 determines whether or not the current resonance frequency Fr is within the range based on the design range information stored in the storage medium 34 (Step S14).

If it is determined that the current resonance frequency Fr is not within the range based on the design range information (Step S14: No), the processor 35 proceeds to step S2. Then, in step S2, the notification control unit 358 causes the notification unit 33 to notify, for example, information indicating that an abnormality occurs in a connection state of the electric cable C, as the information indicating the warning.

On the other hand, if it is determined that the current resonance frequency Fr is within the range based on the design range information (Step S14: Yes), the PLL control unit 357 executes a PLL control for locking the drive frequency F to the current resonance frequency Fr calculated in step S10 based on the latest phase difference (θV-θI) detected after step S9 (Step S15). Then, the processor 35 ends the abnormality determination method.

Specifically, in step S15, when the phase difference detection unit 354 detects that the phase difference (θV-θI) is larger than 0, the PLL control unit 357 lowers the drive frequency F by 1 [Hz], for example. On the other hand, when the phase difference detection unit 354 detects that the phase difference (θV-θI) is smaller than 0, the PLL control unit 357 increases the drive frequency F by 1 [Hz], for example. As a result, the PLL control unit 357 locks the drive frequency F at the current resonance frequency Fr calculated in step S10. Then, the target site grasped between the jaw 45 and the portion of the distal end side Ar1 in the ultrasound probe 46 is treated.

According to the first embodiment described above, the following effects are obtained.

The medical device system 1 according to the first embodiment includes the ultrasound transducer side memory 53 that stores the reference information about the initial characteristics specific to the BLT 52. Then, the medical device system 1 searches for the resonance point of the BLT 52, detects the resonance point information regarding the resonance point, and determines whether or not an abnormality has occurred in the BLT 52 based on the reference information and the resonance point information. In addition, in the first embodiment, the resonance frequency of the BLT 52 is adopted as the reference information and the resonance point information.

That is, by comparing the initial resonance frequency Fr0 at the time of shipping the product with the current resonance frequency Fr obtained by searching for the resonance point, it is possible to accurately determine whether or not the disconnection has occurred in the electric wiring 525. Then, according to the determination, the notification unit 33 notifies the information indicating the warning, thereby making it possible for the operator to recognize that the disconnection has occurred in the electric wiring 525. In addition, according to the determination, the output of ultrasound energy from the ultrasound probe 46 to the target site can also be prohibited (Step S3).

Therefore, it is possible to prevent the treatment of the target site from being performed in a state in which the disconnection occurs in a portion of the electric wiring 525 and the treatment performance is lowered.

In addition, the medical device system 1 according to the first embodiment determines whether the disconnection has occurred in the electric wiring 525 (Step S13) after determining whether or not the ultrasound probe 46 and the BLT 52 that constitute the treatment tool 2 connected to the control device 3 are the controllable types (Step S1).

Therefore, only when the ultrasound probe 46 and the BLT 52 are regular, it is possible to determine whether or not the disconnection has occurred in the electric wiring 525, and the determination can be performed accurately.

In addition, the medical device system 1 according to the first embodiment determines whether or not the disconnection has occurred in the electric wiring 525 (Step S13), and also determines whether the current resonance frequency Fr is within the range based on the design range information (Step S14).

Therefore, for example, it is possible to determine whether or not the connection state of the electric cable C is abnormal.

In addition, in the medical device system 1 according to the first embodiment, the electric wiring 525 is provided on the outer periphery of the substantially columnar shape of the plurality of electrode plates 521 and the plurality of piezoelectric elements 522 integrated with each other. In other words, the electric wiring 525 is provided at a position where the disconnection is likely to occur.

Therefore, when the BLT 52 having such a configuration is used, the abnormality determination method according to the first embodiment is particularly suitable.

Second Embodiment

Next, a second embodiment will be described.
In the following description, the same reference numerals are given to similar configurations as those of the above-described first embodiment, and a detailed description thereof will be omitted or simplified.

In the second embodiment, the reference information stored in the ultrasound transducer side memory 53 and the resonance point information calculated by the resonance point information calculation unit 355 are different from the above-described first embodiment.

Specifically, the reference information according to the second embodiment is information about the initial characteristics specific to the BLT 52, which is measured at the time of shipping of the product of the treatment tool 2, and is information indicating impedance at the resonance point of the BLT 52. Hereinafter, for convenience of explanation, the impedance is referred to as an initial impedance.

In addition, the detection circuit 32 according to the second embodiment detects a voltage value V in the drive signal output from the energy source 31 in addition to the phase signals θV and θI and the current value I. Then, the detection circuit 32 outputs the detected phase signals θV and θI, the current value I, and the voltage value V to the processor 35.

Further, the resonance point information calculation unit 355 according to the second embodiment, when the phase difference is determined to be 0 (Step S10: Yes), in step S11, the resonance point information calculation unit 355 sets the drive frequency F at the time when the phase difference becomes 0 as the current resonance frequency Fr. In addition, the resonance point information calculation unit 355 calculates the impedance based on the current value I and the voltage value V output from the detection circuit 32 at the time when the phase difference becomes 0, and calculates the impedance as the resonance point information. Hereinafter, for convenience of explanation, the impedance is referred to as a current impedance.

Then, the abnormality determination unit 356 according to the second embodiment determines whether or not the disconnection has occurred in the electric wiring 525 based on the current impedance calculated in step S11, the initial impedance based on the reference information read in step S5, and the threshold information stored in the storage medium 34, in step S13.

Specifically, the abnormality determination unit 356 determines whether or not the current impedance is in the range between the initial impedance Im0 (FIG. 8) and an impedance Im0' obtained by adding a threshold ' (FIG. 8) based on the threshold information to the initial impedance Im0. Then, the abnormality determination unit 356 determines that the disconnection has not occurred in the electric wiring 525 when the current impedance is within the range, and determines that the disconnection has occurred in the electric wiring 525 when the current impedance is outside the range.

Even when the impedance is adopted as the reference information and the resonance point information as in the second embodiment described above, the same effect as in the above-described first embodiment is obtained.

Third Embodiment

Next, a third embodiment will be described.
In the following description, the same reference numerals are given to similar configurations as those of the above-described first embodiment, and a detailed description thereof will be omitted or simplified.

In the third embodiment, the reference information stored in the ultrasound transducer side memory 53 and the resonance point information calculated by the resonance point information calculation unit 355 are different from the above-described first embodiment.

Specifically, the reference information according to the third embodiment is information about the initial characteristics specific to the BLT 52, which is measured at the time of shipping of the product of the treatment tool 2, and is information indicating the time from the anti-resonance point Fr' of the BLT 52 to the resonance point Fr when the drive frequency F is swept at a constant speed. Hereinafter, for convenience of explanation, the time is referred to as an initial capture range.

In addition, the resonance point information calculation unit 355 according to the third embodiment calculates the time from when it is determined that the sweep of the drive frequency F is started in step S7 and the current value I has started to rise in step S8 (step S8: Yes) until it is determined that the phase difference becomes 0 in step S10 (step S10: Yes) as resonance point information in step S11. In other words, the resonance point information calculation unit 355 calculates, as resonance point information, the time from when the drive frequency F starts to be swept in step S7 and when the drive frequency reaches the anti-resonance point Fr' to the resonance point Fr. Hereinafter, for convenience of explanation, the time is referred to as a current capture range.

Then, in step S13, the abnormality determination unit 356 according to the third embodiment determines whether or not the disconnection has occurred in the electric wiring 525 based on a current capture range calculated in step S11, a initial capture range based on the reference information read in step S5, and the threshold information stored in the storage medium 34.

Specifically, the abnormality determination unit 356 determines whether the current capture range is within a range between the initial capture range and a capture range obtained by subtracting the threshold based on the threshold information from the initial capture range. Then, the abnormality determination unit 356 determines that the disconnection has not occurred in the electric wiring 525 when the current capture range is within the range, and determines that the disconnection has occurred in the electric wiring 525 when the current capture range is outside the range.

Even when the capture range is adopted as the reference information and the resonance point information as in the third embodiment described above, the same effect as in the above-described first embodiment is obtained.

OTHER EMBODIMENTS

The embodiments for carrying out the disclosure have been described above, but the disclosure should not be limited only to the first to third embodiments.

In the above-described first to third embodiments, the configuration in which the ultrasound energy is applied to the target site is adopted, but the configuration is not limited thereto, and a configuration in which the ultrasound energy and at least one of high frequency energy and thermal energy are applied to the target site may be adopted. Here, "applying high frequency energy to the target site" means passing a high frequency current through the target site. In addition "applying thermal energy to the target site" means that heat generated by the heater or the like is transferred to the target site.

In the above-described first to third embodiments, the threshold based on the threshold information may be configured to be changeable by using the input unit provided in the control device 3 or the like.

In the first to third embodiments described above, the probe type information and the transducer type information are stored in the memories 47 and 53, respectively, but are not limited thereto. For example, a configuration may be adopted in which the handpiece 4 and the ultrasound transducer 5 may each be provided with a resistor having a prescribed resistance value, and the resistance value is read to acquire the probe type information and the transducer type information.

In addition, the flow illustrating the abnormality determination method by the processor 35 is not limited to the order of the processes in the flowchart (FIG. 4) described in the above-described first to third embodiments, and may be changed within a consistent range. For example, a switch separate from the switch 43 is provided in the treatment tool 2 or the control device 3. Then, when the separate switch is pressed, the processor 35 executes the processes of steps S1 to S13. In addition, the processor 35 executes the process of step S14 when the switch 43 is pressed after executing the processes of steps S1 to S13.

According to the disclosure, it is possible to determine the abnormality of the ultrasound transducer.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical device system comprising:
an ultrasound transducer including:
a plurality of electrode plates to which a drive signal is supplied,
a plurality of piezoelectric elements alternately arranged with respect to the plurality of electrode plates, the plurality of piezoelectric elements being configured to generate ultrasound vibrations according to the drive signal,
an electric wiring configured to electrically connect the plurality of electrode plates, which are adjacent to each other, and
a memory configured to store reference information regarding specific initial characteristics; and
a processor operatively coupled to the ultrasound transducer, the processor being configured to:
analyze generated ultrasonic vibrations to determine a resonance point of the ultrasound transducer,
detect resonance point information regarding the determined resonance point, and
determine whether an abnormality has occurred in the ultrasound transducer by comparing the stored reference information and the detected resonance point information, wherein the reference information and the resonance point information each indicate a time from an anti-resonance point of the ultrasound transducer to the determined resonance point when a frequency of the drive signal is at a constant speed.

2. The medical device system according to claim 1, wherein the reference information and the resonance point information each indicate a resonance frequency of the ultrasound transducer.

3. The medical device system according to claim 1, wherein the reference information and the resonance point information each indicate an impedance calculated based on a current value and a voltage value of the drive signal supplied to the ultrasound transducer at the determined resonance point of the ultrasound transducer.

4. The medical device system according to claim 1, further comprising:
an ultrasound probe detachably connected to the ultrasound transducer, the ultrasound probe being configured to transmit the ultrasound vibrations from a proximal end of the ultrasound probe to a distal end of the ultrasound probe; and
a controller detachably connected to the ultrasound transducer, the controller including the processor, wherein the processor is configured to determine the abnormality of the ultrasound transducer after determining that a transducer type of the ultrasound transducer connected to the controller and a probe type of the ultrasound probe are predetermined types.

5. The medical device system according to claim 1, wherein the processor is configured to:
detect a resonance frequency of the ultrasound transducer as the resonance point information, and
determine whether the detected resonance frequency is within a predetermined range based on a pre-designed resonance frequency.

6. The medical device system according to claim 1, wherein:
the plurality of electrode plates and the plurality of piezoelectric elements are alternately arranged to be integrated with each other and to form a columnar shape, and
the electric wiring is provided on an outer periphery of the columnar shape of the plurality of electrode plates and the plurality of piezoelectric elements integrated with each other.

7. The medical device system according to claim 1, wherein the processor is configured to cause a notifier to notify information indicating a warning upon determining that the abnormality has occurred in the ultrasound transducer.

8. The medical device system according to claim 1, further comprising
a handpiece including a handpiece side memory configured to store probe identification information indicating a probe type of the ultrasound probe.

9. An abnormality determination method executed by a processor of a medical device system including an ultrasound transducer, which includes (i) a plurality of electrode plates to which a drive signal is supplied, (ii) a plurality of piezoelectric elements alternately arranged with respect to the plurality of electrode plates, where the plurality of electrode plates are configured to generate ultrasound vibrations according to the drive signal, (iii) an electric wiring configured to electrically connect the plurality of electrode plates, which are adjacent to each other, and (iv) a memory storing reference information regarding specific initial characteristics, the abnormality determination method comprising:
analyzing the generated ultrasonic vibrations to determine a resonance point of the ultrasound transducer;
detecting resonance point information regarding the detected resonance point; and
determining whether an abnormality has occurred in the ultrasound transducer by comparing the stored reference information and the detected resonance point information, wherein the reference information and the resonance point information each indicate a time from an anti-resonance point of the ultrasound transducer to the determined resonance point when a frequency of the drive signal is at a constant speed.

10. The abnormality determination method according to claim 9, wherein:
the medical device system further includes:
an ultrasound probe detachably connected to the ultrasound transducer, the ultrasound probe being configured to transmit the ultrasound vibrations from a proximal end of the ultrasound probe to a distal end of the ultrasound probe; and
a controller detachably connected to the ultrasound transducer, the controller including the processor, and
the method further comprises determining the abnormality of the ultrasound transducer after determining that a transducer type of the ultrasound transducer connected to the controller and a probe type of the ultrasound probe are predetermined types.

11. A non-transitory computer-readable recording medium storing an executable abnormality determination program to be executed by a processor of a medical device system, the medical device system including an ultrasound transducer, which includes (i) a plurality of electrode plates to which a drive signal is supplied, (ii) a plurality of piezoelectric elements alternately arranged with respect to the plurality of electrode plates, wherein the plurality of piezoelectric elements are configured to generate ultrasound vibrations according to the drive signal, (iii) an electric wiring configured to electrically connect the plurality of electrode plates adjacent to each other, and (iv) a memory configured to store reference information regarding specific initial characteristics, the abnormality determination program causing the processor to execute:
analyzing the generated ultrasonic vibrations to determine a resonance point of the ultrasound transducer;
detecting resonance point information regarding the determined resonance point; and
determining whether an abnormality has occurred in the ultrasound transducer by comparing the stored reference information and the detected resonance point information, wherein the reference information and the resonance point information each indicate a time from an anti-resonance point of the ultrasound transducer to the determined resonance point when a frequency of the drive signal is at a constant speed.

* * * * *